United States Patent
Singh et al.

(10) Patent No.: US 10,149,879 B2
(45) Date of Patent: Dec. 11, 2018

(54) ASSOCIATION BETWEEN NEOPTERIN CONCENTRATION AND NEUROVASCULAR CHARGES IN TYPE-2 DIABETES PATIENTS—EFFECT OF AN AYURVEDIC FORMULATION MAINLY CONTAINING BERBERIS ARISTATA

(71) Applicants: Harinder Singh Gill, Bathinda (IN); Gurpreet Singh Gill, Bathinda (IN)

(72) Inventors: Lalji Singh, Hyderabad (IN); Murugesan Ponnavoikko, Tamil Nadu (IN); Gurprit Inder Singh, Bathinda (IN); Govind Prasad Dubey, Varanasi (IN); Veena Pande, Bhimtal (IN); Aruna Agrawal, Varanasi (IN)

(73) Assignees: Gurpreet Singh Gill, Bathinda (IN); Harinder Singh Gill, Bathinda (IN)

( * ) Notice: Subject to any disclaimer, the term of this patent is extended or adjusted under 35 U.S.C. 154(b) by 543 days.

(21) Appl. No.: 14/660,340

(22) Filed: Mar. 17, 2015

(65) Prior Publication Data
US 2016/0158301 A1    Jun. 9, 2016

(30) Foreign Application Priority Data
Dec. 6, 2014 (IN) .......................... 3567/DEL/2014

(51) Int. Cl.
| | | |
|---|---|---|
| A61K 36/31 | (2006.01) | |
| A61K 36/48 | (2006.01) | |
| A61K 36/37 | (2006.01) | |
| A61K 36/29 | (2006.01) | |

(52) U.S. Cl.
CPC .............. A61K 36/48 (2013.01); A61K 36/29 (2013.01); A61K 36/37 (2013.01)

(58) Field of Classification Search
None
See application file for complete search history.

(56) References Cited

U.S. PATENT DOCUMENTS

| | | | | |
|---|---|---|---|---|
| 8,163,312 B2 * | 4/2012 | Krishnan | ............... | A61K 36/00 424/489 |
| 2006/0147561 A1 * | 7/2006 | Pushpangadan | ....... | A61K 36/00 424/734 |
| 2010/0021533 A1 * | 1/2010 | Mazed | ................. | A61K 36/02 424/450 |

* cited by examiner

*Primary Examiner* — Christopher R Tate
*Assistant Examiner* — Randall Winston
(74) *Attorney, Agent, or Firm* — The Webb Law Firm

(57) ABSTRACT

Provided herein are plant based formulations for the prevention and management of diabetic vascular complication The formulation include hydro-alcoholic extract of *Berberis Aristata*, *Trigonella foenum-graceum* and *Salacia parviflora* in an effective dose. Also provided herein are methods of using such formulations.

4 Claims, 1 Drawing Sheet

Following steps are followed -
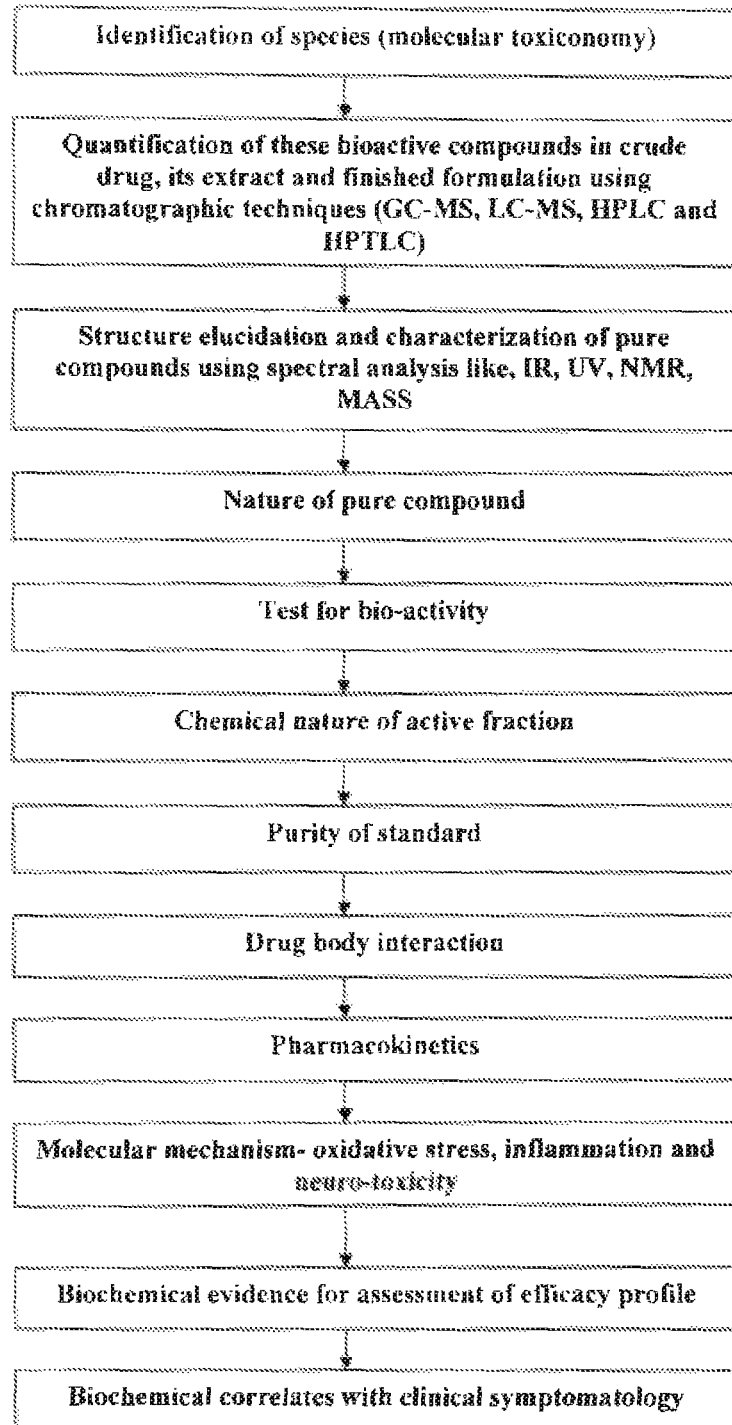

ASSOCIATION BETWEEN NEOPTERIN CONCENTRATION AND NEUROVASCULAR CHARGES IN TYPE-2 DIABETES PATIENTS—EFFECT OF AN AYURVEDIC FORMULATION MAINLY CONTAINING BERBERIS ARISTATA

FIELD OF THE INVENTION

The present invention relates to an Ayurvedic formulation containing hydro-alcoholic extract of *Berberis aristata, Trigonella foenum-graecum* and *Salacia parviflora* effective in decreasing the neopterin concentration thus beneficial in the prevention and management of neuro-vascular complications among type-2 diabetes cases. The present invention may be more advantageous if used in the prevention and management of neuro-vascular inflammation, oxidative injury, dyslipidemia including atherosclerosis and glycemic control in type-2 diabetes patients. The test substance has shown its major therapeutic activity in the prevention of diabetic neuro-vascular complications through its neopterin reducing property as well as its beneficial effect through acting on oxidative stress markers.

BACKGROUND OF THE INVENTION

Neopterin in a product produced by human monocyte-derived macrophages and dendritic cells and is produced in excess amount when neopterin derivatives are upon stimulation with interferon-γ (IFN-γ). In this process neopterin derivatives are able to interfere with reactive oxygen, chlorine and nitrogen species and neopterin itself contributes to oxidative stress. Higher level of neopterin levels and oxidative stress markers are reported in neuro-vascular complications associated with different disease conditions. In neurodegeneration process neopterin concentrations in serum and cerebro-spinal fluid is correlated with the cognitive decline in patients. A significant increase of neopterin concentrations with age is reported in earlier studies. A higher concentration of neopterin with neurodegenerative disorders is perhaps due to immune activation mainly in elderly population. The studies have further supported the view that increased neopterin concentrations are associated with oxidative stress which could underlie an increased demand of anti-oxidants in neurodegenerative conditions particularly in neurovascular complaints associated with diabetes where the oxidative stress play major role in their onset. An early identification of level of neopterin in diabetic patients with neuro-vascular complications is of clinical use as observations are made by various markers that higher neopterin concentrations were associated with reduced residual life span. A positive correlation has been established between neopterin concentration and type-2 diabetes mellitus. In neurodegenerative diseases, neopterin concentrations are correlated with serum concentrations of peroxides and homocysteine among patients with dementia. In such patients the serum concentration of peroxides and homocysteine is recorded among patients with dementia. In such patients the serum concentration of peroxides and neopterin were increased compared to normal people. Further, there is positive correlation between age and concentrations of peroxides, neopterin and homocysteine.

Interaction between neopterin and oxidative stress markers is reported by various markers. Promotion of oxidative stress is a fundamental principle of neopterin release in the process of vascular changes in hyperglycemic condition. Raised serum neopterin levels are found to be associated with severity of disease as well as mortality rate also.

Further, neopterin and TNF-α have also interdependencies, thus TNF-α has been described to enhance the effect of IFN-γ on neopterin synthesis in monocyte-derived macrophages. Neopterin levels are also increased in atherosclerosis in human. Thus application of estimation of neopterin in various diseases provides significant information for prevention and management of disease including neuro-vascular damage associated with diabetes.

Insulin resistance is a key feature of metabolic diseases and is defined as a state that requires more insulin to obtain the biological effects achieved by a lower amount of insulin in the normal state. Thus, any defects in the insulin signaling cascade can cause insulin resistance. Insulin stimulates a signaling network composed of a number of molecules, initiating the activation of insulin receptor tyrosine kinase and phosphorylation of the insulin receptor substrate (IRS) proteins (e.g., IRS-1 and IRS-2). Among several components of the network, the signaling axis of IRS proteins and PI3K, which activates downstream serine/threonine kinases including Akt, regulates most of the metabolic actions of insulin, such as suppression of hepatic glucose production and activation of glucose transport in muscle and adipocytes. It is known that this pathway is impaired at the multiple steps through alterations in the protein levels and activities of the signaling molecules, enzymes, and transcription factors in insulin resistance caused by obesity, a state of increased adiposity.

Risk factors for development of diabetic complications:

Impaired glucose tolerance (IGT) is significantly associated with a 6-10 fold increase in overall risk of progression to type-2 diabetes mellitus. Individuals with IGT have a greater frequency of cardiovascular risk factors like hypertension, dyslipidemia and obesity. Some of the common risk factors like greater duration of diabetes, hypertension, poor metabolic control, smoking, obesity and hyperlipidemia were more prone to develop diabetic complications. Type-2 diabetes mellitus increases the risk of adverse coronary events two-fold in men and four fold in women, due to presence of CHD risk factors.

Further, altered homocysteine, neopterin, leptin, inflammatory bio-markers all are significantly associated with neuro-vascular complications among diabetic patients. The major cardiovascular risk factors affects the endothelium, promoting enhanced endothelial permeability, expression of inflammatory markers and upregulation of particular enzymes that produce oxygen-free radicals, which together lead to the development of a low-grade chronic inflammatory state in the arterial wall. This type of action is responsible for various vascular complications in type-2 diabetes mellitus. Similarly elevated levels of circulating inflammatory markers among type-2 diabetes mellitus are responsible for development of cognitive impairment including development of vascular disease.

Various studies have demonstrated clear benefits of good glycemic control in preventing or retarding the vascular complications in diabetic patients.

Recently, a number of anti-diabetic agents are available to control hyperglycemia but due to long-term/life-long consumption, their use is restricted because of the risk profile. However, no suitable remedial measure is available having activity in prevention and management of neurogenic vascular complications among diabetic patients which badly hampers the quality as well as span of life. The available anti-hyperglycemic drugs include insulin secretagogues (sulfonylureas or meglitinides), insulin sensitizers (metformin or thiazolidinediones) and inhibitors of carbohydrate absorption (a-glucosidase inhibitors) but their long term application causes gastrointestinal disturbances, renal and hepatic impairments, etc. Therefore, there is an urgent need of satisfactory therapeutic modalities free from side-effects. In Ayurveda, various pharmacologic and non-pharmacologic methods have been prescribed for the prevention and management of diabetes and associated complications. Under the scheme Ayurveda as well as other traditional systems of medicine several plant-based drugs have been advocated to manage hyperglycemia.

Taking the lead from Ayurveda, a plant based formulation containing hydro-alcoholic extract of Berberis aristata, Trigonella foenum-graecum and Salecia parvillora in an effective doses determined by us in pre-clinical analysis have been developed and validated for its neopterin lowering property with the object to prevention and treatment of neuro-vascular complications among type-2 diabetes patients. The out come of this study has novelty, innovative and has acceptability for general population as earlier no such type of study is carried out.

OBJECT OF THE INVENTION

An object of present invention is to propose a plant based drug having neopterin lowering property through which diabetic neuro-vascular complications can be prevented and also the development of vascular complications can be delayed in diabetes patients.

Another object of present invention is to propose a plant based drug showing better therapeutic potential in neuro-protection in diabetes patients.

Further, object is to develop a plant based drug that can inhibit fat mobilizing enzymes and can enhance lipolysis in hyperglycemic condition.

Yet another object of present invention is to propose an Ayurvedic formulation exerting anti-oxidant activity among type-2 diabetes patients.

Still another object of present study is to propose a plant based drug showing anti-inflammatory role by reducing IL-2. TNF-α and IFN-γ in diabetic cases as inflammation is a major feature in vascular biology of atherosclerosis causing atherothrombosis resulting in coronary artery disease. Thus an adverse coronary stroke can be prevented.

Still further object of present invention is to propose a botanical formulation beneficial in the prevention and management of neurogenic dementia/cognitive deficits among type-2 diabetes patients.

The foregoing has outlined some of the pertinent objectives of the present invention. However, these objectives should not be construed to be merely illustrative of some of the more prominent features and applications of the intended interventions. Many more therapeutic potentials of the test substance can be achieved through this invention. As synergism also the test drug has immunomodulatory, regulating altered neuro-chemical markers and better neurologic effects.

Accordingly, other objects and a full understanding of the invention and the detailed description of the preferred embodiment in addition to the scope of invention are to be defined through the claims defined in the application.

Thus the other objects and advantages of present invention are apparent from the ensuing description.

BRIEF DESCRIPTION OF THE INVENTION

According to this invention there is provided a plant based formulation for the prevention and management of vascular complications particularly neuro-vascular damage in diabetic patients through its neopterin reducing property. The test drug contained the hydro-alcoholic extract of Berberis aristata, Trigonella foenum-graecum and Salacia parviflora in effective doses along with additional additive in trace amount.

At the outset of the description, which follows, it is to be understood that the ensuing description only illustrate a particular form of the invention. However, such a particular form is only an exemplary embodiment and the teachings of the invention are not intended to be taken restrictively.

BRIEF DESCRIPTION OF THE ACCOMPANYING DRAWINGS

FIG. 1 shows the specific steps were followed for the isolation of active compound to determine biological property of test drug so that a novel formulation can be developed that can fulfill our objects.

DETAILED DESCRIPTION OF THE INVENTION

For the purpose of promoting an understanding of the principles of the invention, reference is now to be made to the embodiments illustrates and the specific language would be used to describe the same. It is nevertheless to be understood that no limitations of the scope of the invention is hereby intended, such alterations and further modifications in the illustrated bag and such further applications of the principles of the invention as illustrated therein being contemplated as would normally occur to one skilled in the art to which the invention relates.

The hydro-alcoholic extract of three medicinal plant candidates Berberis aristata, Trigonella foenum-graecum and Salacia parviflora prepared using 70:30 ratio water and alcohol respectively has been utilized for the development of present Ayurvedic formulation. The water utilized for extraction was decontaminated for any type of bacterial or abnormal growth by using reverse osmosis plant. The active molecules present in plant extracts were separated and quantified by applying HPLC, HPTLC and NMR procedures. In order to establish the neopterin lowering property of test formulation a mechanism based pre-clinical documentation was prepared. The therapeutic potential of test drug was determined by conducting various experimental and clinical trials.

The neopterin lowering property of test drug was determined on the basis of mode of action of plant extracts separately as well as in combined form along with various targets involved in vascular complications in diabetes cases. Similarly the beneficial role of test drug was also assessed mainly through its anti-oxidant activity, lipolysis and insulin sensitivity improving effects, anti-inflammatory and anti-atherosclerotic activity of test formulation. Further, the synergistic effects of test drug were also evaluated.

Before utilizing the test drug for human consumption the pre-clinical safety and efficacy profile of single plant candidate extract as well as in combined form was conducted following standard norms. The biological property of test formulation was validated in streptozotocin (STZ) induced diabetes animal model which also helped in evaluation of vascular complications caused due to diabetes. The effect of test drug was assessed on glucose levels, insulin level, glycosylated hemoglobin, and pro-inflammatory cytokines, and the most important bio-marker neopterin including various neuro-psychological assessments. The mechanism based study clearly indicated the neopterin decreasing potential of test formulation which exerted neuro-protective activity, better glycemic control, anti-atherosclerotic, anti-inflammatory, anti-oxidant effects in STZ induced diabetes among the animals. Further, its therapeutic activity has also been validated in neurogenic dementia and other cognitive deficits associated with diabetes mellitus.

Extraction procedure/process adopted in the present study:

The shade dried rhizome of *Berberis aristata*, seeds of *Trigonella foenum-graecum* and roots of *Salacia parviflora* were separately utilized for obtaining their extract. The hydro-alcoholic extract of the plants were utilized to determine the presence of molecules/active compound in both the plant extracts. The molecular characterization of plant extracts were done through IR and NMR.

The extraction was done at a specific temperature 70°-80° and the pH of the solution was maintained by 5-6.

According to this invention there is provided a plant based Ayurvedic formulation showing efficacy in the prevention and management of diabetic neuro-vascular complications through its neopterin lowering property. The present test drug comprises of following three plant extract—

| Name of the plants | Part used |
| --- | --- |
| 1. *Berberis aristata* (Daru-Haridra) | Root |
| 2. *Trigonella foenum-graecum* (Methi) | Seeds |
| 3. *Salacia parviflora* (Saptchakra) | Root |

Preferably the aforesaid plant extracts are taken in the following doses in the test formulation—

| Name of the plants | Dose |
| --- | --- |
| 1. *Berberis aristata* | 400-750 mg/day |
| 2. *Trigonella foenum-graecum* | 250-500 mg/day |
| 3. *Salacia parviflora* | 300-550 mg/day |

The test formulation also comprises known additive, may be vitamins, salts, filler (for capsulation or to prepare syrup) and binders if required, will be in trace amount.

Thus a known additional additive in a known amount is added to prepare final formulation and the reference is made in capsule form.

However, it would be apparent that the test formulation may also be prepared in tablet or syrup form.

Preferably but without implying any limitation the present preparation comprises—

| Name of the plants | Dose |
| --- | --- |
| 1. *Berberis aristata* | 375 mg/day |
| 2. *Trigonella foenum-graecum* | 250 mg/day |
| 3. *Salacia parviflora* | 325 mg/day |

In human increased concentration of neopterin in circulation and also in urine has been assessed in various clinical conditions. The generated data support the view that higher neopterin concentration produces heavy reaction oxygen species causing more oxidative injury that requires more anti-oxidant therapeutic agents in neurodegenerative conditions particularly when associated with diabetic patients. A number of studies have indicated that the concentration of neopterin were found significantly higher in Alzheimer's disease patients showing low scores of mini-mental state examination. Further, a significant correlation was observed between level of neopterin and TNF-α, IL-2. A possible correlation is also noticed with severity of dementia and level of neopterin. This type of study appears to be much important and early detection of neopterin concentration among diabetic patients with dementia or other cognitive deficits will be helpful in launching prevention and management strategies. A better mental health can be achieved out of such studies. As reported aging is associated with immune system activation which may lead to the increased production of peroxides, the anti-oxidant and immuno-modulatory measure will definitely provide a better result in protection from neurodegeneration through increasing anti-oxidant vitamins and modifying the stimulation of immuno-competent cells. The involved mechanism of action may be that neopterin derivatives are able to interfere with reactive oxygen, chlorine and nitrogen species and neopterin itself causing oxidative stress and the method which will reduce the neopterin concentration will prevent the cognitive decline particularly associated with diabetic patients by preventing oxidative injury and monitoring of cell-mediated immune response. Thus study conducted by us appears very Important that changes in neopterin content detected in blood stream of patients with diabetes with dementia or neuro-vascular involvement, suggests its pathogenesis is considered to be confined to the brain. Further, it is hypothesized that as age advances among diabetics, there will be more association with immune system activation, increased production of peroxides and such people will need heavy medication for the management of their complaints. Thus, present study providing newer remedial measure has proven its beneficial role on new bio-markers associated with diabetes causing neuro-vascular complications.

The present test formulation has been prepared out of hydro-alcoholic extract of three plants i.e. *Berberis aristata, Trigonella foenum-graecum* and *Salacia parviflora* in effective doses. This novel formulation has been proven for its neopterin lowering property in diabetes condition with the object of prevention and treatment of vascular complications particularly neuro-vascular abnormalities in type-2 diabetes patients.

As enough knowledge exists indicating the role of lifestyle modification in the management of diabetes but the role of residual confounding by unknown factors cannot be eliminated/ignored. It is observed that there is close association between neopterin along with inflammatory markers IL-2 and TNF-α is responsible for vascular damage among diabetes patients. The test formulation was found beneficial in reducing IL-2, TNF-α and also the CRP in type-2 diabetes patients. It is pointed out that inflammation is a major feature in the vascular biology of atherosclerotic lesions. In all the stages i.e. fatty streak, plaque-rupture and thrombosis, inflammatory process play a pivotal role and link between inflammation and cardiovascular pathology/event and neurovascular changes is very strong. In the present study efforts have been made to prevent or delay the vascular complications through control of inflammatory process by decreasing the TNF-α, IL-2 and IFN-γ and decreasing neopterin level in diabetic patients.

1. *Berberis aristata* (Daruharidra), also known as Indian Barberry or Tree Turmeric, belongs to the family Berberidaceae. It is evergreen shrub and is found in the temperate and sub-tropical regions of Asia, Europe, and America. *B. aristata* is native to the Himalayas in India and Nepal. The root bark contains berberine, quaternary ammonium salt of isoquinoline alkaloid. Root of *Berberis*

*aristata* contain alkaloids i.e. Berbamin, Berberin, oxyberberin, aromoline, palmatine, taxilamine, protoberberin, bisisoquinoline, oxycanthine, epiberberin, dehydrocaroline, jatrorhizine, columbamine 5,6 karachine, 7 dihydrokarachine, pseudopalmatine chloride pseudoberbarin chloride. *Berberis aristata* having 2.23% of berberin.

Berberin is an alkaloid isolated from *Berberis aristata* and it is used as an anti-amoebic, bitter tonic, berberin posses CNS activity particularly inhibit MAO-A (The enzyme which are involved in degradation of nor-epinephrine and serotonine) acute administration of Berberin (5 mg/kg ip) in mice resulted in increased level of nor-epinephrine 31%, serotonin 47% and dopamine 31% in whole brain. Berberin also act as an anti-inflammatory drug. Berberin and palmatine belongs to isoquinoline alkaloid group specially found in roots and stems of *berberis* species and shows various pharmacological activity like anti-fungal, anti-diarrhoeal, anti-hypertensive, anti-arrythemic, hypolipidemic, anti-inflammatory, anti-microbial, anti-prolofertive, renoprotective and have potent anti-diabetic activity. Other compound palmatine also exert anti-diabetic activity. Diabetic animal treated with Berberin posses positive effect on endogenous oxidative stress markers by improving catalase, superoxide dismutase, glutathione peroxidase, and glutathione activity.

2. *Trigonella foenum-graecum* (Methi): This plant belongs to family papplionaceae and it is an aromatic 30-60 cm tall plant, annual and cultivated throughout the country. The endosperm of seed are medicinally active and it is rich in galactomannon, and mature seeds contain various component like amino acids, fatty acids, vitamins and saponins which are responsible for anti-hyperglycemic activity. It contains large quantity of folic acid, diosgenin, gitogenin, neogitogenin, neogigogenin trigogenin fixed oil and identified alkaloid such as trigonelline and choline, quercetin is present as flavanoid which posses antioxidant activity. *Trigonella foenum-graecum* act as an Immunomodulatory, chemo-preventive, anti-oxidant and gastroprotective agent, and exerts anti-diabetic, anti-hyperglycemic and anti-inflammatory activity. This plant shows anti-diabetic effect due to presence of 4-hydroxyisoleucine. *Trigonella foenum-graecum* posses anti-hyperglycemic activity due to presence of an alkaloid Trigonelline, trigocoumarine, and caumarine.

3. *Salacia parviflora* (Saptachakra): This plant belongs to Celastraceae including Hippocrataceae family. It is climbing shrub with blackish branches. Root and bark is used for medicinal purposes. It contains sitosterol, mangiferin, catechine, salaciquinane, triterpenoids etc. Mangiferin, salacinol and kotanelol are active constituents of this plant and potent alpha-glucosidase inhibitors that have been shown to decrease serum glucose levels. The active constituent present in the plant also inhibits aldose reductase activity thereby delaying the development of diabetic complications particularly diabetic neuropathy and nephropathy. It also has anti-obesity, anti-inflammatory role.

Experimental Evidence

Effect of *Berberis aristata* on Urine Volume and Glyceuira

| Animal Group | Urine volume (ml) | Glyceuria |
| --- | --- | --- |
| Normoglycaemic | 6.13 ± 1.26** | – |
| Hyperglycemic | 15.20 ± 3.12** | +++ |
| H.G. + Metformin | 8.95 ± 1.70* | + |
| H.G. + Pioglitazone | 13.23 ± 1.18** | ++ |
| H.G. + *Berberis aristata* L | 12.23 ± 1.40 | ++ |
| H.G. + *Berberis aristata* H | 8.95 ± 1.00* | ++ |

(+++) abundant;
(++) moderate,
(+) mild,
(−) complete absence

Urine was collected from each group separately by using animal metabolic cage, volume of urine collected was measured and glucose executed in urine was detected by Benedict reagent. In which 1 ml of urine and 3 ml of B.R. are added and boiled for 5 minute. The change in color was observed as Red (+++), green coloration (++) yellow coloration (+) and unchanged (−).

Anti-Hyperglycemic Activity of *Berberis aristata*—Weekly Assessment of Plasma Glucose

| Groups | 0th Day | 7th Day | 14th Day |
| --- | --- | --- | --- |
| Normoglycaemic | 86.17 ± 10.85*** | 88.9 ± 6.39 | 88.57 ± 9.85*** |
| Hyperglycemic | 170.83 ± 13.41### | 175.67 ± 14.38### | 185.00 ± 7.35### |
| H.G. + Metformin | 169.83 ± 10.03### | 148.67 ± 8.85***### | 118.83 ± 8.75***### |
| H.G. + Pioglitazone | 170.17 ± 12.55*** | 153.83 ± 15.68***## | 140.17 ± 6.25**## |
| H.G. + *Berberis aristata* L | 169.17 ± 12.12### | 160.83 ± 9.49*### | 149.50 ± 10.21***### |
| H.G. + *Berberis aristata* H | 171.33 ± 13.40### | 155.83 ± 7.60**### | 136.67 ± 8.45***### |

*### $P < 0.001$, $P < 0.01$, *$P < 0.05$, percentile changes in plasma glucose was calculated.

Low dose=100 mg/kg; High dose=200 mg/kg

This table shows reduction in glucose level on $7^{th}$ day but significant reduction was observed on $14^{th}$ day which was comparable as the standard drug metformin, all this conclusion reported that the test drug having anti-hyperglycemic property.

Effect of *Berberis aristata* on Body Weight

| Groups | 0th Day | 7th Day | 14th Day |
| --- | --- | --- | --- |
| Normoglycaemic | 202.30 ± 6.20 | 210.17 ± 7.30*** | 225.25 ± 8.70*** |
| Hyperglycemic | 195.20 ± 3.21 | 170.70 ± 6.23 | 150.27 ± 6.13 |
| H.G. + Metformin | 207.25 ± 6.44 | 180.21 ± 2.21 | 175.00 ± 3.00 |
| H.G. + Pioglitazone | 200.00 ± 4.65 | 178.80 ± 4.00 | 169.13 ± 2.84 |
| H.G. + *Berberis aristata* L | 205.13 ± 2.12 | 176.69 ± 3.84 | 160.84 ± 3.11 |
| H.G. + *Berberis aristata* H | 204.64 ± 3.14 | 175.15 ± 3.19 | 158.81 ± 3.24 |

Body weight was checked and monitored weekly and tabulated diabetes mellitus is associated with characteristics of body weight can due to several reason and test drug exhibit protection towards the loss of body weight.

Insulin Secretagogues Property of *Berberis aristata* in Diabetic Animals

| Groups | Insulin (pg/L) |
|---|---|
| Normoglycaemic | 120.38 ± 19.18 |
| Hyperglycemic | 99.16 ± 10.00 |
| H.G. + Metformin | 109.24 ± 12.13 |
| H.G. + Pioglitazone | 105.31 ± 9.10 |
| H.G. + *Berberis aristata* L | 111.00 ± 10.19 |
| H.G. + *Berberis aristata* H | 114.18 ± 10.19 |

In diabetes secretion of insulin is inhibited but after the administration of test drug the secretion of insulin can be enhanced.

Restoration of Glycogen in Liver and Skeletal Muscle by *Berberis aristata* Glycogen Content (nM/Mg of Tissue)

| Groups | Liver | Skeletal muscle |
|---|---|---|
| Normoglycaemic | 1311.41 ± 160.95 | 98.98 ± 10.61 |
| Hyperglycemic | 750.51 ± 59.65 | 35.16 ± 7.43 |
| H.G. + Metformin | 1095.03 ± 63.10 | 86.98 ± 12.80 |
| H.G. + Pioglitazone | 975.00 ± 43.14 | 42.02 ± 7.26 |
| H.G. + *Berberis aristata* L | 985.14 ± 36.41 | 55.15 ± 12.00 |
| H.G. + *Berberis aristata* H | 1089.13 ± 59.11 | 87.00 ± 10.88 |

Stored glycogen was visualized using PAS staining as purple particle, purple color representing glycogen were found to be abundant. Treated with *Berberis aristata* prevent glycogen breakdown due to diabetes, (glycogen content rose up in liver & skeletal muscle after treatment).

Regulation of Key Enzymes in Gluconeogenesis by *Berberis aristata*

| | G-6-P (μm/min/mg of protein) | | F,1-6 bisphosphate (μm/min/mg of protein) | |
|---|---|---|---|---|
| Animal Group | Liver | Kidney | Liver | Kidney |
| Normo-glycaemic | 47.88 ± 3.15 | 33.71 ± 4.94 | 30.05 ± 2.16 | 28.15 ± 4.09 |
| Hyperglycemic | 78.81 ± 5.25 | 50.26 ± 9.11 | 47.56 ± 4.59 | 34.10 ± 4.34 |
| H.G + Metformin | 57.49 ± 8.17 | 41.85 ± 7.71 | 34.59 ± 4.90 | 29.67 ± 5.60 |
| H.G. + Pioglitazone | 68.56 ± 7.51 | 45.08 ± 4.76 | 44.33 ± 4.29 | 31.78 ± 3.71 |
| H.G. + *Berberis aristata* L | 63.17 ± 6.23 | 43.55 ± 6.07 | 42.33 ± 3.73 | 33.08 ± 3.85 |
| H.G. + *Berberis aristata* H | 57.14 ± 6.85 | 43.07 ± 7.73 | 36.53 ± 3.81 | 29.56 ± 5.93 |

Reduction in activity of the enzyme resulted in the decline of glucose level (high dose of test drug 200 mg/kg) exhibit reduction in activity of both enzyme.

Neoptein Decreasing Property of *Berberis aristata* in Experimental Diabetes

| | Neopterin (nmol/L) | | |
|---|---|---|---|
| Animal Group | 0 days | $7^{th}$ day | $14^{th}$ Day |
| Normoglycaemic | 7.82 ± 1.28 | 6.88 ± 2.79 | 6.01 ± 2.82 |
| Hyperglycemic | — | 10.01 ± 2.11 | 12.27 ± 2.19 |
| H.G. + Metformin | — | 8.90 ± 1.87 | 9.11 ± 1.39 |
| H.G. + Pioglitazone | — | 9.13 ± 2.10 | 8.02 ± 2.01 |
| H.G. + *Berberis aristata* L | — | 8.13 ± 2.87 | 9.04 ± 1.03 |
| H.G. + *Berberis aristata* H | — | 9.02 ± 2.13 | 9.04 ± 3.14 |

Adiponectin Enhancing Property of *Berberis aristata* in Experimental Diabetes

| | Adiponectin (pg/ml) | | |
|---|---|---|---|
| Animal Group | 0 days | $7^{th}$ day | $14^{th}$ Day |
| Normoglycaemic | 13.32 ± 2.06 | 12.88 ± 2.79 | 14.01 ± 2.82 |
| Hyperglycemic | — | 7.01 ± 2.11 | 6.27 ± 2.19 |
| H.G. + Metformin | — | 6.90 ± 1.87 | 6.11 ± 1.39 |
| H.G. + Pioglitazone | — | 7.13 ± 2.10 | 8.02 ± 2.01 |
| H.G. + *Berberis aristata* L | — | 8.13 ± 2.87 | 9.04 ± 1.03 |
| H.G. + *Berberis aristata* H | — | 9.02 ± 2.13 | 11.04 ± 3.14 |

Anti-Hyperlipidemic Activity of *Berberis aristata*

| | Cholesterol (mg/dl) | | |
|---|---|---|---|
| Animal Group | 0 days | $7^{th}$ day | $14^{th}$ Day |
| Normoglycaemic | 62.06 ± 7.80 | 61.17 ± 5.97 | 63.00 ± 5.16 |
| Hyperglycemic | 103.67 ± 9.50 | 115.53 ± 8.41 | 111.00 ± 8.29 |
| H.G. + Metformin | 110.33 ± 9.55 | 100.00 ± 5.63 | 88.17 ± 4.79 |
| H.G. + Pioglitazone | 112.33 ± 7.50 | 94.23 ± 8.23 | 81.41 ± 9.94 |
| H.G. + *Berberis aristata* L | 113.05 ± 11.45 | 106.75 ± 16.82 | 101.83 ± 8.77 |
| H.G. + *Berberis aristata* H | 105.74 ± 15.70 | 95.50 ± 17.97 | 89.17 ± 6.96 |

*Berberis aristata* especially at high dose 200 mg/kg significantly reduced cholesterol on $7^{th}$ day of drug treatment. Both doses high and low showed reduction in cholesterol level on $14^{th}$ day of treatment, at high dose could bring reduction in triglycerides levels on $7^{th}$ day of treatment.

Anti-Hyperlipidemic Activity of *Berberis aristata* on Triglycerides

| | Triglycerides (mg/dl) | | |
|---|---|---|---|
| Animal Group | 0 days | $7^{th}$ day | $14^{th}$ Day |
| Normoglycaemic | 68.67 ± 6.54 | 71.58 ± 10.71 | 67.50 ± 4.33 |
| Hyperglycemic | 136.78 ± 8.97 | 156.65 ± 13.73 | 168.57 ± 6.50 |
| H.G. + Metformin | 134.77 ± 14.06 | 123.32 ± 9.51 | 102.50 ± 11.75 |
| H.G. + Pioglitazone | 133.35 ± 09.77 | 117.50 ± 9.02 | 71.30 ± 6.26 |
| H.G. + *Berberis aristata* L | 131.01 ± 10.52 | 135.00 ± 7.42 | 142.50 ± 9.02 |
| H.G. + *Berberis aristata* H | 137.33 ± 7.77 | 122.17 ± 11.26 | 112.30 ± 10.15 |

Triglycerides level being reduced on $7^{th}$ day of treatment at high dose of test drug.

Lipoprotein Profile and Assessment of Atherosclerosis Following Test Formulation Treatment

| Animal Group | HDL-c | VLDL-c | LDL-c | Atherogenic Index | Anti-atherogenic index |
|---|---|---|---|---|---|
| Normoglycaemic | 35.23 ± 2.95 | 15.10 ± 0.47 | 15.67 ± 3.28 | — | 23.59 ± 4.90 |
| Hyperglycemic | 22.50 ± 2.87 | 35.31 ± 2.08 | 76.19 ± 7.17 | 4.90 ± 0.71 | — |
| H.G. + Metformin | 27.68 ± 3.51 | 22.10 ± 3.15 | 41.38 ± 4.26 | 2.66 ± 0.44 | 6.34 ± 3.17 |
| H.G. + Pioglitazone | 31.44 ± 2.85 | 17.86 ± 2.05 | 35.11 ± 7.29 | 2.20 ± 0.35 | 10.02 ± 5.23 |
| H.G. + Test formulation (150 mg/kg) | 23.33 ± 3.88 | 30.10 ± 2.60 | 51.40 ± 4.51 | 3.51 ± 0.44 | 2.22 ± 3.43 |
| H.G. + Test formulation (300 mg/kg) | 25.00 ± 2.67 | 14.06 ± 2.83 | 43.11 ± 2.94 | 2.92 ± 0.22 | 5.53 ± 3.27 |

Treated with test formulation leading to increase the level of HDL-c & decreased cholesterol level in atherogenic lipoprotein (LDL-c & VLDL-c) leading to suppress atherogenic index and improve anti-atherigenic Index.

Reduction in Free Fatty Acids Following Test Formulation Treatment

Treated with test formulation reported FFA elevation in tissues and plasma of diabetic rats Reduction in hypertrophy of Adipocyte on Treated with Test Formulation

| | Free Fatty Acid (FFA) mg/100 g of tissue | | |
|---|---|---|---|
| Animal Group | Plasma (mg/L) | Heart | Liver |
| Normoglycaemic | 60.83 ± 4.60 | 350.00 ± 20.67 | 480.33 ± 25.52 |
| Hyperglycemic | 111.50 ± 6.92 | 596.67 ± 53.58 | 998.50 ± 85.50 |
| H.G. + Metformin | 87.67 ± 7.68 | 446.83 ± 39.65 | 777.83 ± 53.14 |
| H.G. + Pioglitazone | 69.00 ± 5.60 | 379.17 ± 22.06 | 522.67 ± 37.75 |
| H.G. + Test formulation (150 mg/kg) | 100.50 ± 6.47 | 541.83 ± 39.89 | 888.67 ± 60.97 |
| H.G. + Test formulation (300 mg/kg) | 77.17 ± 5.96 | 513.83 ± 39.89 | 822.00 ± 34.31 |

| Animal Group | Adipocyte cell area (μm) |
|---|---|
| Normoglycaemic | 80.10 ± 10.17 |
| Hyperglycemic | 198.33 ± 12.37 |
| H.G. + Metformin | 146.24 ± 10.85 |
| H.G. + Pioglitazone | 136.31 ± 13.53 |
| H.G. + Test formulation (150 mg/kg) | 164.66 ± 7.51 |
| H.G. + Test formulation (300 mg/kg) | 113.13 ± 8.00 |

Attenuation of Oxidative Stress Following Treatment with Test Formulation—Restriction of SOD

| Animal Group | Brain | Heart | Liver | Kidney | Pancrease |
|---|---|---|---|---|---|
| Normoglycaemic | 30.17 ± 1.98 | 24.00 ± 3.30 | 23.67 ± 2.01 | 21.17 ± 2.32 | 9.20 ± 0.21 |
| Hyperglycemic | 18.00 ± 2.67 | 11.50 ± 3.59 | 12.33 ± 1.25 | 14.00 ± 2.00 | 6.76 ± 0.48 |
| H.G. + Metformin | 19.83 ± 3.56 | 14.33 ± 5.13 | 15.33 ± 0.86 | 16.00 ± 2.37 | 7.01 ± 0.46 |
| H.G. + Pioglitazone | 19.33 ± 3.66 | 15.83 ± 5.83 | 13.50 ± 1.76 | 16.67 ± 1.86 | 6.91 ± 0.22 |
| H.G. + Test formulation (150 mg/kg) | 23.27 ± 3.82 | 17.67 ± 9.41 | 19.50 ± 2.94 | 22.33 ± 2.16 | 7.19 ± 0.37 |
| H.G. + Test formulation (300 mg/kg) | 24.95 ± 3.65 | 20.12 ± 9.90 | 23.33 ± 1.16 | 26.67 ± 3.50 | 7.78 ± 0.31 |

Attenuation of Oxidative Stress Following Treatment with Test Formation—Reduction in TBARS Formation

| Animal Group | Brain | Heart | Liver | Kidney | Pancrease |
|---|---|---|---|---|---|
| Normoglycaemic | 45.00 ± 3.70 | 33.48 ± 2.95 | 40.50 ± 3.00 | 37.54 ± 2.94 | 50.17 ± 5.11 |
| Hyperglycemic | 58.37 ± 3.21 | 84.53 ± 2.93 | 103.00 ± 11.12 | 59.33 ± 3.27 | 88.00 ± 8.21 |
| H.G. + Metformin | 48.08 ± 3.42 | 62.33 ± 4.81 | 80.83 ± 9.17 | 56.74 ± 5.07 | 83.17 ± 7.24 |
| H.G. + Pioglitazone | 52.66 ± 3.55 | 61.83 ± 4.52 | 82.50 ± 2.84 | 56.33 ± 7.93 | 87.67 ± 7.41 |
| H.G. + Test formulation (150 mg/kg) | 50.17 ± 3.46 | 50.67 ± 7.55 | 53.57 ± 3.79 | 54.33 ± 4.67 | 78.00 ± 8.67 |
| H.G. + Test formulation (300 mg/kg) | 43.09 ± 2.92 | 44.81 ± 9.43 | 43.83 ± 4.57 | 49.21 ± 3.67 | 66.00 ± 4.05 |

Attenuation of Oxidative Stress by Treatment with Test Formulation for GPx Activity

| Animal Group | Brain | Heart | Liver | Kidney | Pancrease |
|---|---|---|---|---|---|
| Normoglycaemic | 9.76 ± 3.40 | 10.36 ± 2.72 | 12.64 ± 4.57 | 9.64 ± 3.56 | 51.33 ± 5.46 |
| Hyperglycemic | 5.04 ± 2.45 | 4.45 ± 2.62 | 6.81 ± 3.84 | 5.74 ± 3.90 | 22.17 ± 4.99 |
| H.G. + Metformin | 7.54 ± 2.29 | 5.80 ± 2.63 | 7.32 ± 4.27 | 6.45 ± 3.25 | 26.50 ± 2.87 |
| H.G. + Pioglitazone | 7.66 ± 2.28 | 5.08 ± 3.52 | 7.72 ± 3.58 | 8.60 ± 3.51 | 25.83 ± 6.00 |

-continued

| Animal Group | Brain | Heart | Liver | Kidney | Pancrease |
|---|---|---|---|---|---|
| H.G. + Test formulation (150 mg/kg) | 7.68 ± 2.23 | 7.17 ± 2.92 | 7.47 ± 2.65 | 6.81 ± 3.80 | 28.50 ± 6.17 |
| H.G. + Test formulation (300 mg/kg) | 8.77 ± 2.62 | 8.25 ± 2.20 | 9.42 ± 4.01 | 9.09 ± 3.48 | 33.73 ± 3.75 |

Restoration of GSH Content Following Test Formulation Treatment

| Animal Group | Brain | Heart | Liver | Kidney | Pancrease |
|---|---|---|---|---|---|
| Normoglycaemic | 1.49 ± 0.20 | 1.47 ± 0.18 | 1.61 ± 0.19 | 1.61 ± 0.21 | 18.37 ± 0.91 |
| Hyperglycemic | 0.85 ± 0.18 | 0.95 ± 0.19 | 0.99 ± 0.30 | 0.96 ± 0.20 | 4.99 ± 0.98 |
| H.G. + Metformin | 1.33 ± 0.24 | 1.30 ± 0.25 | 1.49 ± 0.26 | 1.30 ± 0.22 | 7.40 ± 0.70 |
| H.G. + Pioglitazone | 1.39 ± 0.27 | 1.39 ± 0.24 | 1.44 ± 0.23 | 1.29 ± 0.20 | 6.18 ± 0.66 |
| H.G. + Test formulation (150 mg/kg) | 0.92 ± 0.35 | 0.96 ± 0.43 | 0.91 ± 0.30 | 1.25 ± 0.19 | 9.98 ± 2.86 |
| H.G. + Test formulation (300 mg/kg) | 1.44 ± 0.20 | 1.32 ± 0.34 | 1.31 ± 0.36 | 1.27 ± 0.40 | 13.73 ± 1.10 |

Aldose Reductase Activity and Glycation of Hemoglobin Following Test Formulation Treatment

| Groups | Hb (g/dl) | Glycated Hb (mg/g of Hb) | Aldose reductase ($\mu$M of NADPH oxidized/g of protein) |
|---|---|---|---|
| Normoglycaemic | 11.05 ± 0.62 | — | 2.03 ± 0.09 |
| Hyperglycemic | 8.00 ± 0.25 | 0.49 ± 0.05 | 3.85 ± 0.15 |
| H.G. + Metformin | 10.06 ± 0.06 | 0.44 ± 0.04 | 2.60 ± 0.75 |
| H.G. + Pioglitazone | 10.09 ± 1.85 | 0.53 ± 0.07 | 2.99 ± 0.04 |
| H.G. + Test formulation (150 mg/kg) | 9.08 ± 0.60 | 0.60 ± 0.03 | 3.30 ± 0.25 |
| H.G. + Test formulation (300 mg/kg) | 10.08 ± 0.48 | 0.45 ± 0.02 | 2.60 ± 0.60 |

Hepato-Protective Effect of Test Formulation

| Animal Group | SGOT (U/L) | SGPT (U/L) | ALP (U/L) | ACP (U/L) | LDH (U/L) |
|---|---|---|---|---|---|
| Normoglycaemic | 42.49 ± 3.40 | 13.00 ± 1.02 | 112.20 ± 2.13 | 9.00 ± 1.32 | 101.50 ± 10.84 |
| Hyperglycemic | 90.10 ± 1.25 | 37.25 ± 3.00 | 145.00 ± 14.00 | 13.00 ± 1.10 | 190.21 ± 25.13 |
| H.G. + Metformin | 60.00 ± 5.00 | 24.25 ± 2.12 | 142.00 ± 6.00 | 12.05 ± 0.68 | 145.11 ± 15.00 |
| H.G. + Pioglitazone | 72.00 ± 5.71 | 27.00 ± 3.00 | 139.50 ± 3.15 | 11.95 ± 1.00 | 160.00 ± 15.00 |
| H.G. + Test formulation (150 mg/kg) | 70.85 ± 3.15 | 30.00 ± 1.50 | 112.13 ± 5.15 | 11.10 ± 1.20 | 134.00 ± 9.19 |
| H.G. + Test formulation (300 mg/kg) | 59.75 ± 3.12 | 20.00 ± 3.16 | 110.21 ± 5.04 | 11.59 ± 0.78 | 124.75 ± 14.14 |

Effect of Test Formulation on Renal Function

| Groups | Creatinine (mg/dl) | Urea (mg/dl) |
|---|---|---|
| Normoglycaemic | 1.08 ± 0.10 | 35.18 ± 1.10 |
| Hyperglycemic | 5.71 ± 0.58 | 60.00 ± 2.00 |
| HG + Metformin | 3.18 ± 0.05 | 45.45 ± 5.25 |
| H.G. + Pioglitazone | 3.20 ± 0.09 | 48.00 ± 2.00 |
| H.G. + Test formulation (150 mg/kg) | 3.20 ± 0.04 | 49.19 ± 3.00 |
| H.G. + Test formulation (300 mg/kg) | 2.98 ± 0.03 | 38.16 ± 3.00 |

Cell Viability Assay in βTC6 Insulinoma Cell Lime Following—

| Dose | Berberin | Palmatine | Dose | Test formulation |
|---|---|---|---|---|
| Control | 100.00 ± 0.20 | 100.00 ± 0.20 | Control | 100.00 ± 0.20 |
| 1 pM | 97.95 ± 1.12 | 97.96 ± 1.10 | 1 pg/ml | 98.03 ± 3.18 |
| 10 pM | 96.99 ± 2.20 | 97.50 ± 2.05 | 10 pg/ml | 96.46 ± 2.10 |
| 100 pM | 94.60 ± 2.45 | 96.52 ± 2.70 | 100 pg/ml | 94.70 ± 2.31 |
| 1 nM | 90.89 ± 1.42 | 94.80 ± 1.32 | 1 ng/ml | 93.25 ± 1.24 |
| 10 nM | 88.65 ± 2.60 | 91.66 ± 1.60 | 10 ng/ml | 90.18 ± 2.00 |
| 100 nM | 86.30 ± 1.67 | 84.45 ± 1.30 | 100 ng/ml | 86.01 ± 1.49 |
| 1 μM | 73.75 ± 2.90 | 83.20 ± 1.90 | 1 μg/ml | 83.51 ± 1.10 |
| 10 μM | 67.89 ± 1.65 | 81.98 ± 1.70 | 10 μg/ml | 80.35 ± 1.70 |

Anti-Oxidant Activity in βTC6 Insulinoma Cell Challenged with $H_2O_2$ Berberin and Quercetin—

|  | Berberin | | | Quercetin | |
| --- | --- | --- | --- | --- | --- |
| Dose | Pre-incubate | Co-incubated | Dose | Pre-incubated | Co-incubated |
| Control | 55.64 ± 0.50 | 55.64 ± 0.50 | Control | 55.64 ± 0.50 | 55.64 ± 0.50 |
| 1 pg/ml | 61.60 ± 2.00 | 59.70 ± 2.00 | 0.1 pM | 64.00 ± 2.10 | 60.31 ± 2.71 |
| 10 pg/ml | 65.18 ± 1.98 | 64.14 ± 2.04 | 1 pM | 68.38 ± 1.79 | 67.11 ± 2.71 |
| 100 pg/ml | 67.05 ± 2.45 | 67.40 ± 1.43 | 10 pM | 77.51 ± 2.06 | 70.10 ± 2.30 |
| 1 ng/ml | 74.40 ± 1.40 | 76.57 ± 1.50 | 100 pM | 81.63 ± 1.50 | 80.72 ± 1.20 |
| 10 ng/ml | 77.69 ± 2.10 | 85.90 ± 2.00 | 1 nM | 87.59 ± 1.95 | 90.44 ± 1.94 |

Berberin at a dose of 10 ng/ml is found to be non-toxic to the cells

Anti-Oxidant Activity in βTC6 Insulinoma Cell Challenged with $H_2O_2$ Berberin and Palmatine—

|  | Berberin | | Palmatine | |
| --- | --- | --- | --- | --- |
| Dose | Pre-incubated | Co-incubated | Pre-incubated | Co-incubated |
| Control | 55.54 ± 1.50 | 55.54 ± 1.50 | 55.54 ± 1.50 | 55.54 ± 1.50 |
| 1 pM | 57.52 ± 0.80 | 54.53 ± 1.67 | 55.32 ± 1.48 | 56.95 ± 3.60 |
| 10 pM | 58.90 ± 2.87 | 54.79 ± 2.95 | 61.67 ± 2.10 | 57.04 ± 2.00 |
| 0.1 nM | 60.12 ± 3.40 | 56.02 ± 2.82 | 65.18 ± 1.95 | 60.10 ± 1.41 |
| 1 nM | 61.70 ± 1.60 | 59.80 ± 1.30 | 67.05 ± 2.40 | 61.75 ± 2.16 |
| 10 nM | 64.20 ± 1.65 | 60.75 ± 2.16 | 69.58 ± 2.55 | 65.83 ± 0.81 |

Berberin and Palmatine Showed Mild Protection Against $H_2O_2$ Induced Cellular Oxidative Damaged Cell Viability Assay in 3T3-L1 Cells

| Dose | Berberin | Palmatine | Dose | *Berberis aristata* (Extract) |
| --- | --- | --- | --- | --- |
| Control | 100.00 ± 0.34 | 100.00 ± 0.21 | Control | 100.00 ± 1.10 |
| 10 pM | 99.50 ± 1.50 | 100.00 ± 0.10 | 10 pg/ml | 100.00 ± 2.00 |
| 100 pM | 99.99 ± 2.80 | 99.99 ± 0.54 | 100 pg/ml | 99.70 ± 2.30 |
| 1 nM | 99.88 ± 0.91 | 99.45 ± 0.48 | 1 ng/ml | 98.53 ± 2.70 |
| 10 nM | 98.25 ± 1.20 | 98.30 ± 1.80 | 10 ng/ml | 98.34 ± 2.73 |
| 100 nM | 97.69 ± 1.09 | 98.90 ± 1.06 | 100 ng/ml | 96.96 ± 1.15 |
| 1 μM | 90.68 ± 2.05 | 95.15 ± 1.58 | 1 μg/ml | 92.40 ± 3.20 |
| 10 μM | 75.12 ± 2.85 | 89.26 ± 1.30 | 10 μg/ml | 89.53 ± 1.10 |
| 100 μM | 62.54 ± 4.20 | 83.10 ± 1.67 | 100 μg/ml | 87.06 ± 0.99 |

Berberin and Palmatine at the dose of 1 μM is found to be non-toxic and *Berberis aristata* extract at the dose of 1 μg/ml is found to be non-toxic to the cell.

Anti-Oxidant Activity in 3T3-L1 Cells Challenged with $H_2O_2$ Berberin and Palmatine

|  | Berberin | | Palmatine | |
| --- | --- | --- | --- | --- |
| Dose | Pre-incubated | Co-incubated | Pre-incubated | Co-incubated |
| Control | 50.00 ± 1.30 | 50.00 ± 1.30 | 50.00 ± 1.30 | 50.00 ± 1.30 |
| 10 pM | 52.01 ± 2.80 | 56.00 ± 3.35 | 53.18 ± 3.25 | 54.85 ± 2.20 |
| 100 pM | 55.76 ± 2.80 | 58.96 ± 1.20 | 55.13 ± 1.50 | 57.18 ± 1.20 |
| 1 nM | 59.95 ± 2.10 | 61.80 ± 1.80 | 57.00 ± 1.25 | 59.87 ± 2.70 |
| 10 nM | 61.13 ± 1.05 | 63.00 ± 1.60 | 61.40 ± 0.25 | 63.00 ± 1.10 |
| 100 nM | 64.25 ± 2.30 | 63.38 ± 2.10 | 67.25 ± 2.25 | 65.75 ± 1.40 |

Berberin and palmatine showed mild protection against $H_2O_2$ induced cellular oxidative damaged Anti-Oxidant Activity in 3T3-L1 Cells Challenged with $H_2O_2$ Berberin and Quercetin

|  | Berberin | | | Quercetine | |
| --- | --- | --- | --- | --- | --- |
| Dose | Pre-incubated | Co-incubated | Dose | Pre-incubated | Co-incubated |
| Control | 49.00 ± 0.25 | 49.00 ± 0.25 | Control | 50.00 ± 0.40 | 50.00 ± 0.40 |
| 10 pg/ml | 55.00 ± 2.00 | 53.00 ± 2.50 | 0.1 pM | 61.00 ± 3.00 | 57.30 ± 1.70 |

-continued

| | Berberin | | | Quercetine | |
|---|---|---|---|---|---|
| Dose | Pre-incubated | Co-incubated | Dose | Pre-incubated | Co-incubated |
| 100 pg/ml | 58.00 ± 1.70 | 57.80 ± 2.50 | 1 pM | 65.00 ± 1.70 | 65.00 ± 2.75 |
| 1 ng/ml | 64.00 ± 1.90 | 65.15 ± 1.99 | 10 pM | 75.15 ± 2.99 | 68.01 ± 2.75 |
| 100 ng/ml | 67.40 ± 3.70 | 70.80 ± 3.25 | 100 pM | 88.60 ± 2.60 | 78.70 ± 3.50 |
| 100 ng/ml | 75.00 ± 4.15 | 77.50 ± 2.95 | 1 nM | 94.15 ± 1.70 | 88.40 ± 1.90 |

Berberin showed potent protection against $H_2O_2$ induced cellular oxidative damage. However, the activity of positive standard quercetin is found to be superior even at lower concentration.

Anti-Oxidant Activity in L6 Cells Challenged with $H_2O_2$ Berberin and Palmatine

| | Berberin | | Palmatine | |
|---|---|---|---|---|
| Dose | Pre-incubated | Co-incubated | Pre-incubated | Co-incubated |
| Control | 60.10 ± 3.40 | 60.10 ± 3.40 | 60.10 ± 3.40 | 60.10 ± 3.40 |
| 10 pM | 59.80 ± 6.60 | 62.10 ± 4.40 | 58.70 ± 4.70 | 56.13 ± 6.40 |
| 100 pM | 60.40 ± 8.50 | 63.97 ± 8.52 | 63.30 ± 3.16 | 60.50 ± 5.50 |
| 1 nM | 63.70 ± 7.25 | 66.10 ± 5.67 | 66.12 ± 5.85 | 63.91 ± 5.04 |
| 10 nM | 68.60 ± 4.50 | 69.40 ± 5.00 | 66.70 ± 3.12 | 67.53 ± 8.12 |
| 100 nM | 72.81 ± 5.70 | 72.40 ± 3.03 | 70.00 ± 5.95 | 71.70 ± 6.16 |

Berberin and palmatine showed mild protection against $H_2O_2$ induced cellular oxidative damaged.

Anti-Oxidant Activity in L6 Cells Challenged with $H_2O_2$—Berberin and Quercetin

| | Berberin | | | Quercetine | |
|---|---|---|---|---|---|
| Dose | Pre-incubated | Co-incubated | Dose | Pre-incubated | Co-incubated |
| Control | 61.10 ± 1.70 | 61.10 ± 1.70 | Control | 61.10 ± 1.70 | 61.10 ± 1.10 |
| 10 pg/ml | 63.50 ± 1.00 | 60.40 ± 2.20 | 0.1 pM | 63.60 ± 1.50 | 57.50 ± 1.80 |
| 100 pg/ml | 69.40 ± 2.00 | 66.12 ± 2.70 | 1 pM | 68.02 ± 1.40 | 65.05 ± 2.80 |
| 1 ng/ml | 71.12 ± 1.12 | 70.07 ± 2.95 | 10 pM | 75.12 ± 3.50 | 70.36 ± 2.96 |
| 10 ng/ml | 78.98 ± 1.90 | 75.14 ± 0.90 | 100 pM | 87.90 ± 1.60 | 78.18 ± 2.99 |
| 100 ng/ml | 83.70 ± 1.70 | 77.51 ± 1.70 | 1 nM | 95.15 ± 0.99 | 88.64 ± 1.99 |

Berberin and quercetine showed potent protection against $H_2O_2$ induced cellular oxidative damage. However, the activity of positive standard quercetin were found to be superior even at lower concentration.

Anti-Diabetic Activity in L6-Myotubes by Berberin, Palmatine and *Berberis aristata* Extract

| Dose | Berberin | Palmatine | Dose | *Berberis aristata* (Extract) |
|---|---|---|---|---|
| Control | 1.00 ± 0.12 | 1.00 ± 0.12 | Control | 1.00 ± 0.12 |
| Insulin | 3.70 ± 0.15 | 3.70 ± 0.15 | Insulin | 3.70 ± 0.15 |
| 1 nM | 1.38 ± 0.08 | 1.58 ± 0.10 | 20 ng/ml | 1.60 ± 0.12 |
| 5 nM | 1.78 ± 0.08 | 1.78 ± 1.10 | 100 ng/ml | 1.74 ± 0.08 |
| 25 nM | 1.98 ± 0.08 | 2.12 ± 0.09 | 500 ng/ml | 1.98 ± 0.08 |
| 125 nM | 2.30 ± 0.08 | 2.35 ± 0.12 | 2 µg/ml | 2.28 ± 0.07 |
| 625 nM | 2.50 ± 0.10 | 2.60 ± 0.10 | 10 µg/ml | 2.46 ± 0.08 |

Berberin, palmatine and *Berberis aristata* extract showed accelerated glucose consumption in differentiated L6-myotubes which is dose dependent.

Clinical Evidence

Results & Observations:

The clinical trial following test formulation in diabetes patients indicated significant improvement in neuropsychological as well as various biochemical parameters. At the initial level strong association between insulin resistance, type-2 diabetes mellitus and cognitive decline was observed. In other words a poor mental performance due to impairment in glucose metabolism has been noticed. A significant high concentration of serum neopterin was found to be associated with insulin resistance and cognitive function in diabetes patients. The test formulation exerted neuro-protective effects when evaluated on various neuropsychophysiological parameters in diabetes patients. Thus it is proven that some of the molecules or active constituents present in plant materials used in the test formulation has a role in preventing the neuro-toxic effects of glucose metabolism impairment and improved the cognitive function. It is concluded that test formulation has potentiality in preventing the neuro-vascular damage caused due to prolonged hyperglycemia.

TABLE 1

Pattern of various factors involved with type-2 diabetes patients showing cognitive deficits

| Parameters | Sex | No. of cases - 161 (male-93; female-68) | Vascular complications % | | Receiving oral anti-hyperglycemic |
|---|---|---|---|---|---|
| Age (Years) | M | 53.97 ± 8.24 | Retinopathy | 12 | 100% 79% oral anti-diabetic drugs, 4% insulin dependent, 4% diet control + Ayurvedic drug |
| | F | 57.35 ± 9.06 | | | |
| BMI (index) | M | 31.24 ± 3.97 | Neuropathy | 26 | |
| | F | 29.82 ± 4.73 | | | |
| Duration of onset of diabetes | M | 15.28 years | Nephropathy | 22 | |
| | F | 12.62 years | | | |
| HbA1c (%) | M | 10.64 ± 2.08 | | | |
| | F | 9.48 ± 3.11 | | | |
| Insulin (mU/mL) | M | 8.87 ± 4.01 | | | |
| | F | 7.98 ± 3.88 | | | |
| Total cholesterol (mg/dl) | M | 204.80 ± 38.94 | | | |
| | F | 192.75 ± 42.80 | | | |
| Triglycerides (mg/dl) | M | 239.73 ± 69.25 | | | |
| | F | 245.73 ± 72.68 | | | |
| LDL-c (mg/dl) | M | 119.82 ± 13.91 | | | |
| | F | 114.87 ± 17.22 | | | |
| HDL-c (mg/dl) | M | 43.20 ± 2.85 | | | |
| | F | 45.82 ± 5.13 | | | |

TABLE 2

Cognitive deficit associated with type-2 diabetes patients and its prevention and management by test formulation.

| Treatment groups | Parameters | Initial | After 6 months | After 12 months | Comp. Initial vs After 12 months |
|---|---|---|---|---|---|
| Conventional Anti-diabetic drug + Placebo (N = 82) | MMSE | 15.87 ± 6.22 | 15.29 ± 4.90 | 16.01 ± 5.13 | $P > 0.02$ |
| | DSS | 42.17 ± 13.90 | 41.68 ± 10.23 | 41.98 ± 12.04 | $P > 0.05$ |
| | Attention span | 7.02 ± 2.45 | 6.11 ± 1.64 | 6.64 ± 1.20 | $P > 0.02$ |
| | Word recall delayed | 4.97 ± 1.04 | 4.83 ± 0.89 | 4.98 ± 0.75 | $P > 0.05$ |
| Conventional Anti-diabetic drug + Test formulation (N = 88) | MMSE | 14.32 ± 5.87 | 16.25 ± 4.13 | 17.98 ± 4.13 | $P < 0.05$ |
| | DSS | 39.55 ± 12.62 | 43.15 ± 10.04 | 47.22 ± 11.02 | $P < 0.02$ |
| | Attention span | 6.90 ± 1.66 | 8.22 ± 2.71 | 8.91 ± 2.13 | $P < 0.05$ |
| | Word recall delayed | 3.91 ± 0.87 | 4.87 ± 1.32 | 5.14 ± 1.39 | $P < 0.01$ |

MMSE: Mini mental state examination;
DSS: Digit symbol substitution

TABLE 3

Effect of test formulation on memory span among type-2 diabetes patients

| Treatment groups | Memory span (Score) | | | | | | Comp. Initial vs. after 12 months | |
|---|---|---|---|---|---|---|---|---|
| | Initial | | After 6 months | | After 12 months | | | |
| | STM | LTM | STM | LTM | STM | LTM | STM | LTM |
| Conventional Anti-diabetic drug + Placebo (N = 82) | 6.45 ± 1.79 | 4.52 ± 1.82 | 6.82 ± 1.35 | 4.65 ± 1.37 | 6.91 ± 1.82 | 4.37 ± 0.90 | $P > 0.02$ | $P > 0.05$ |
| Conventional Anti-diabetic drug + Test formulation (N = 88) | 6.22 ± 1.14 | 4.13 ± 1.20 | 7.25 ± 2.01 | 5.03 ± 1.18 | 8.04 ± 1.08 | 5.87 ± 1.38 | $P < 0.02$ | $P < 0.05$ |

STM: Short Term Memory;
LTM: Long Term Memory

TABLE 4

Improvement in functional activity and dementia score following test formulation treatment in diabetes patients.

| Treatment groups | Parameters | Initial | After 6 months | After 12 months | Comp. Initial vs After 12 months |
|---|---|---|---|---|---|
| Conventional Anti-diabetic drug + Placebo (N = 82) | FAQ (Score) | 15.62 ± 4.13 | 15.39 ± 3.88 | 14.59 ± 3.72 | P > 0.02 |
| | HDS (Score) | 16.01 ± 3.77 | 16.29 ± 3.88 | 15.64 ± 2.95 | P > 0.05 |
| Conventional Anti-diabetic drug + Test formulation (N = 88) | FAQ (Score) | 14.96 ± 4.83 | 16.31 ± 3.05 | 17.55 ± 3.11 | P < 0.01 |
| | HDS (Score) | 13.58 ± 2.95 | 15.68 ± 3.75 | 16.83 ± 3.82 | P < 0.05 |

FAQ = Functional Activity Questionnaire;
HDS = Hasegawa Dementia Scale

TABLE 5

Decrease in inflammatory markers following test drug treatment in diabetes patients.

| Treatment groups | Parameters | Initial | After 6 months | After 12 months | Comp. Initial vs After 12 months |
|---|---|---|---|---|---|
| Conventional Anti-diabetic drug + Placebo (N = 82) | hsCRP (mg/L) | 6.29 ± 1.02 | 5.82 ± 1.35 | 6.19 ± 1.82 | P > 0.05 |
| | IL-6 (pg/ml) | 2.64 ± 0.87 | 2.52 ± 0.91 | 2.41 ± 0.73 | P > 0.02 |
| | TNF-α (pg/ml) | 838.90 ± 226.85 | 901.44 ± 197.60 | 887.32 ± 224.13 | P > 0.02 |
| Conventional Anti-diabetic drug + Test formulation (N = 88) | hsCRP (mg/L) | 5.97 ± 1.93 | 4.55 ± 1.13 | 3.72 ± 0.92 | P < 0.01 |
| | IL-6 (pg/ml) | 2.73 ± 0.74 | 2.14 ± 0.97 | 1.47 ± 0.82 | P < 0.05 |
| | TNF-α (pg/ml) | 922.47 ± 289.32 | 773.45 ± 128.81 | 662.90 ± 146.59 | P < 0.01 |

TABLE 6

Decrease in neopterin concentration following test formulation treatment in type-2 diabetes patients showing neuro-vascular changes

| | Neopterin (nmol/L) | | | Comp. Initial vs After 12 months |
|---|---|---|---|---|
| Treatment groups | Initial | After 6 months | After 12 months | |
| Conventional Anti-diabetic drug + Placebo (N = 60) | 22.48 ± 4.39 | 21.88 ± 3.97 | 20.88 ± 2.99 | P > 0.02 |
| Conventional Anti-diabetic drug + Test formulation (N = 58) | 24.90 ± 3.87 | 21.08 ± 4.11 | 19.20 ± 4.06 | P < 0.05 |

TABLE 7

Adiponectin enhancing effect of test formulation treatment in type-2 diabetes patients

| | Adiponectin (pg/ml) | | | Comp. Initial vs After 12 months |
|---|---|---|---|---|
| Treatment groups | Initial | After 6 months | After 12 months | |
| Conventional Anti-diabetic drug + Placebo (N = 82) | 7.13 ± 2.10 | 6.91 ± 2.82 | 7.02 ± 2.03 | P > 0.05 |

TABLE 7-continued

Adiponectin enhancing effect of test formulation treatment in type-2 diabetes patients

| Treatment groups | Adiponectin (pg/ml) | | | Comp. Initial vs After 12 months |
|---|---|---|---|---|
| | Initial | After 6 months | After 12 months | |
| Conventional Anti-diabetic drug + Test formulation (N = 88) | 6.97 ± 2.34 | 8.93 ± 2.68 | 9.39 ± 3.04 | $P < 0.01$ |

Example-I

When the Hydro-alcoholic extract of *Berberis aristata* in the dose of 250 mg/kg b.w. was administered to STZ induced hyperglycemic rats showed reduction in neopterin concentration indicating better glycemic control than the non-treatment group of animals. The active compound present in plant extract berberin and palmitin showed potent anti-oxidant activity in βTC6 cells challenged with hydrogen peroxide.

Example-II

When the hydro-alcoholic extract of *Berberis aristata* in the dose of 150 mg/kg b.w. and *Trigonella foenum-graecum* in the dose of 100 mg/kg b.w. given in combined form exerted significant increase in glutathione content and decrease in TBARS with important in other oxidative stress markers in comparison to disease control group. It prevented apoptosis and decreased insulin secreting cell population. The neuro-vascular damage was prevented through its anti-oxidant and anti-inflammatory activity.

Example-III

When the hydro-alcoholic extract of *Berberis aristata* (60 mg/kg) and *Salacia parviflora* in the dose of 140 mg/kg b.w. was mixed and given to STZ induced hyperglycemic rats regulated carbohydrate metabolism by retaining glycogen content in the liver and muscle. Thus the carbohydrate metabolism with test substance is due to its potentiality to protect β-cell mass in the pancreas thereby improving plasma insulin level, improved glycemic index.

Example-IV

When the hydro-alcoholic extract of *Berberis aristata* in the dose of 75 mg/kg b.w. and *Trigonella foenum-graecum* in the dose of 75 mg/kg b.w. to STZ treated diabetic rats have shown neopterin lowering activity and also reduced the glycosylated hemoglobin in hyperglycemic rats, thus has neuro-protective effects.

Example-V

When the hydro-alcoholic extract of *Berberis aristata* in the dose of 75 mg/kg b.w., *Salacia parviflora* in the dose of 75 mg/kg b.w. and *Trigonella foenum-graecum* in the dose of 50 mg/kg b.w. given in combined form to STZ induced diabetic rats exerted potential role in reducing neopterin concentration, improvement in altered oxidative stress markers and also showed neuro-protective effects by improving learning process (memory status) of the animals.

In any combination of test substance prepared out of above three plants were found non-toxic on toxicological studies.

Example-VI

After determination of safety profile of test formulation/single plant extract the test formulation was taken for human consumption to evaluate its beneficial role in the prevention and management of neuro-vascular complications in diabetes patients. The test formulation reduced the neopterin level of the diabetic patients exerting ability of test substance (*Berberis aristata* 350 mg/day and *Salacia parviflora* 425 mg/day) containing active bio-molecules exerted anti-oxidant property and improved cognitive function by enhancing memory, attention and overall mental performance in diabetes patients thus beneficial in the prevention and management of neurogenic dementia among diabetes patients.

Example-VII

When the hydro-alcoholic extract of *Berberis aristata* in the dose of 375 mg/day and *Trigonella foenum-graecum* in the dose of 425 mg/day was given to diabetes patients showing cognitive impairment (poor memory and attention including behavioral abnormality) revealed reduced neuro-inflammation Indicating improved neuro-vascular degeneration caused due to hyperglycemia.

Example-VIII

The test formulation has shown decrease in lipid accumulation when the hydro-alcoholic extract of *Berberis aristata* (450 mg/day) and *Salacia parviflora* (425 mg/day) was given to type-2 diabetes patients, reduced the neopterin level and elevated oxidative stress markers. This combination is having potentiality in reducing HbA1c and inflammatory markers IFN-γ, IL-2, and TNF-α in diabetic patients.

Example-IX

The test formulation containing hydro-alcoholic extract of *Salacia parviflora* (375 mg/day) and *Trigonella foenum-graecum* (450 mg/day) containing active compounds has activity on cellular glucose consumption in pre-adipocyte cells and adipocytes as it accelerated glucose transpiring potency, decreased the neopterin level and increases the adiponectin concentration in diabetes patients.

Example-X

When the hydro-alcoholic extract of *Berberis aristata* in the dose of 300 mg/day, *Trigonella foenum-graecum* in the dose of 250 mg/day and *Salacia parviflora* in the dose of 350 mg/day was administered to diagnosed patients of type-2 diabetes mellitus showed anti-hyperglycemic, anti-hyperlipidemic with amelioration of cognitive functions through its neopterin lowering activity and adiponectin enhancing effects among type-2 diabetes patients involving mechanism of mitigating oxidative stress, promoting insulin secretion, Inhibiting gluconeogenesis and glycogenolysis thereby regulating blood glucose in diabetic patients and preventing diabetic complications. The most important activity of present test formulation revealed that it regulated lipogenic markers like LPL, FAS and reduces neopterin level suggesting improved mental ability through improved neuro-vascular changes and improved atherogenic dyslipidemia among diabetes patients. The test substance contains numerous compounds mediating several activities prevented neuro-vascular complications through its anti-oxidant, anti-inflammatory and neopterin reducing effects among diabetes cases. Thus the use of present test formulation will be beneficial for the treatment of diabetes and its complications particular neuro-vascular changes rather than only its active anti-diabetic role. The study conducted by present team has generated scientific evidence for therapeutic uses of our traditional knowledge which supports our claims also.

The test formulation exerted prevention/delayed development of vascular complications among type-2 diabetes patients through its neopterin lowering property. It improved the cognitive deficits particularly memory, attention and behavior complaints of diabetic patients as the test formulation is a potent anti-oxidant agent prevented neuron damage and enhanced neuronal plasticity among diabetic patients.

We claim:

1. A method of preventing or treating diabetic vascular complications comprising administering to a patient in need thereof a formulation comprising effective amounts of hydro-alcoholic extracts of *Berberis Aristata, Trigonella foenum-graceum* and Salacia *parviflora*.

2. The method as claimed in claim 1 wherein the method comprises administering the formulation to the patient such that the following amounts of each extract are provided:

| Name of the plants | Dose |
| --- | --- |
| 1. *Berberis aristata* | 400-750 mg/day |
| 2. *Trigonella foenum-graecum* | 250-500 mg/day |
| 3. Salacia *parviflora* | 300-550 mg/day |

3. The method as claimed in claim 1, wherein the method comprises administering the formulation to the patient such that the following amounts of each extract are provided:

| Name of the plants | Dose |
| --- | --- |
| 1. *Berberis aristata* | 375 mg/day |
| 2. *Trigonella foenum-graecum* | 250 mg/day |
| 3. Salacia *parviflora* | 325 mg/day |

4. The method as claimed in claim 1, wherein the formulation has anti-hyperglycemic, anti-hyperlipidemic, anti-neuro-inflammatory and adiponectin enhancing effects with the result that the formulation prevents cognitive impairment caused due to hyperglycemia.

* * * * *